(12) United States Patent
Otte et al.

(10) Patent No.: US 7,949,620 B2
(45) Date of Patent: May 24, 2011

(54) METHOD AND DEVICE FOR DETECTING CLUSTERS AMONGST DATA ARRANGED IN ORDERS FOR CLUSTER CREATION AND REMOVAL BASED ON CONDITIONAL PROBABILITIES BETWEEN CLUSTERS

(75) Inventors: Clemens Otte, Munich (DE); Rudolf Sollacher, Eching (DE); Volker Tresp, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 578 days.

(21) Appl. No.: 11/378,640

(22) Filed: Mar. 20, 2006

(65) Prior Publication Data

US 2006/0224549 A1 Oct. 5, 2006

(30) Foreign Application Priority Data

Mar. 18, 2005 (DE) .......................... 10 2005 012 665

(51) Int. Cl.
*G06E 1/00* (2006.01)
*G06E 3/00* (2006.01)
*G06F 15/18* (2006.01)
*G06G 7/00* (2006.01)
*G06N 3/02* (2006.01)

(52) U.S. Cl. ........................................................ 706/15

(58) Field of Classification Search .................... 706/15
See application file for complete search history.

(56) References Cited

U.S. PATENT DOCUMENTS

2003/0009467 A1* 1/2003 Perrizo ........................ 707/100

OTHER PUBLICATIONS

Gary, B. and Orlowska, M. "CCAIIA: Clustering Categorical Attributes into Interesting Association Rules", Pacific-Asia Conference on Knowledge Discovery and Data Mining, 1998, pp. 132-143.*
Giuffrida, G., Cooper, L. and Chu, W. "A Scalable Bottom-Up Data Mining Algorithm for Relational Databases", Proc. Scientific and Statistical Database Management,1998, pp. 206-209.*
A. Hyvärinen et al.; "Independent Component Analysis", Independent Component Analysis, Wiley Interscience, 2001, pp. 1-7.
P. Andritsos et al., "LIMBO: A Scalable Algorithm to Cluster Categorical Data", CSRG Technical Report 467, University of Toronto, Dept. of Computer Science, 2003, pp. 1-41.

* cited by examiner

*Primary Examiner* — Donald Sparks
*Assistant Examiner* — Li-Wu Chang
(74) *Attorney, Agent, or Firm* — Staas & Halsey LLP

(57) ABSTRACT

After initial clusters having only one component are formed, a conditional probability $P(C_i|C'_k)$ is determined for the cluster $C_i$ being included in an order on condition that cluster $C'_k$ is included in the order. If $P(C_i|C'_k)$ is greater than a first threshold value $S_1$, a new cluster $C_n$ having all the components of clusters $C_i$, $C'_k$ is formed and the operations are repeated until no new clusters are formed.

16 Claims, 2 Drawing Sheets

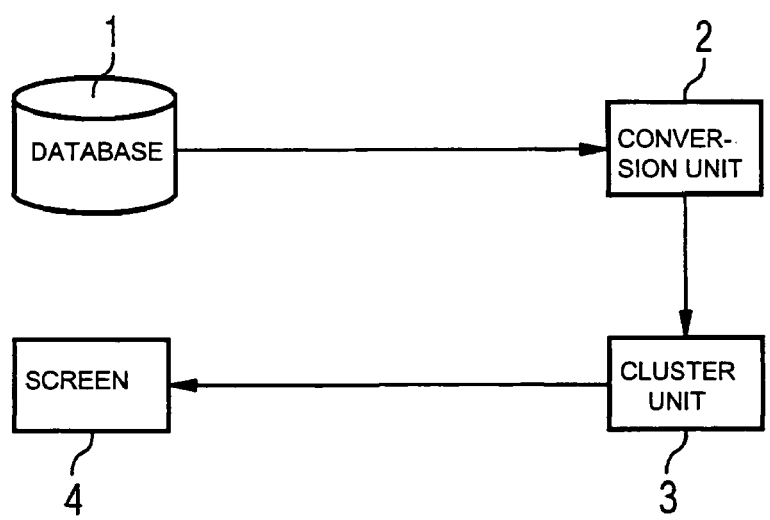

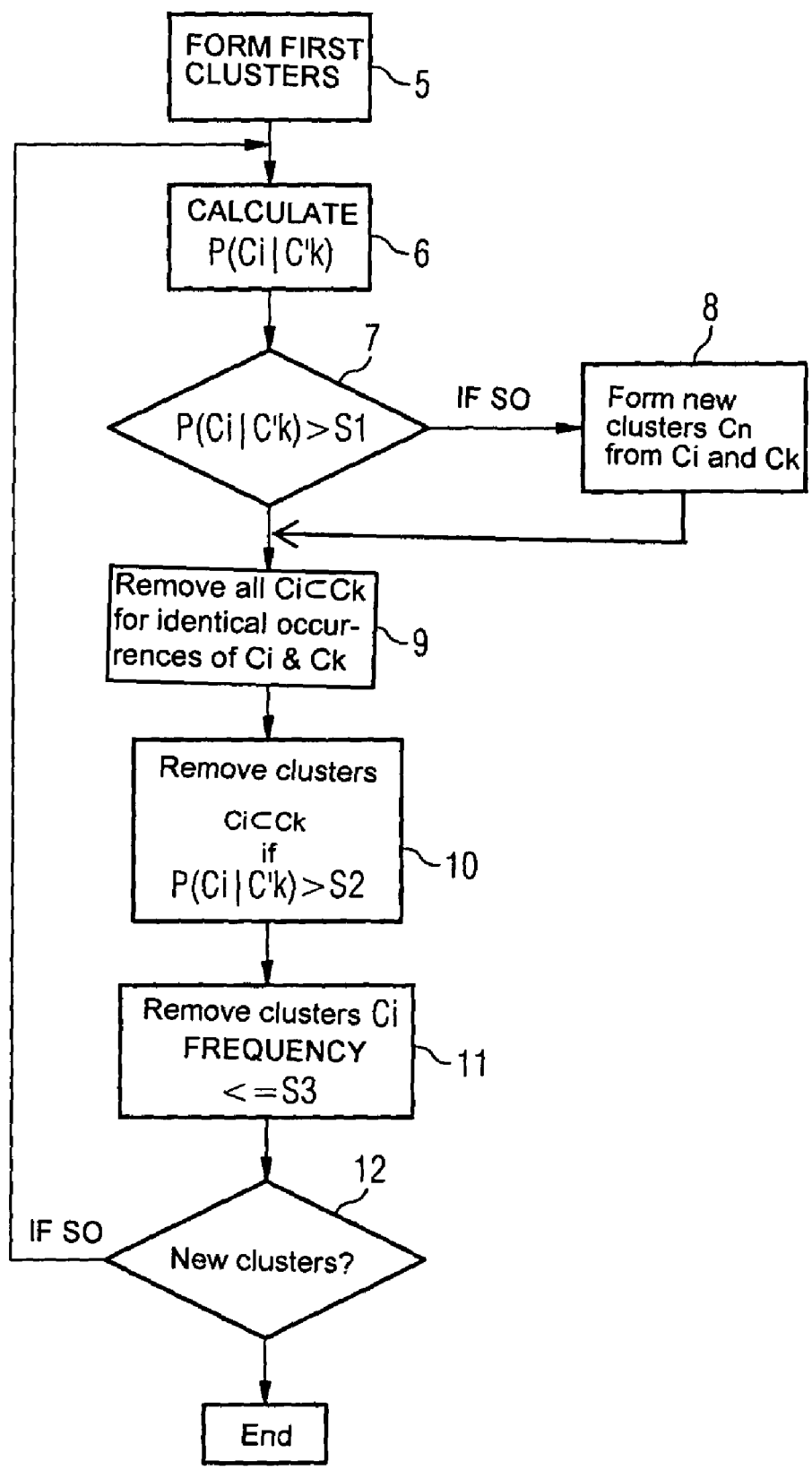

METHOD AND DEVICE FOR DETECTING CLUSTERS AMONGST DATA ARRANGED IN ORDERS FOR CLUSTER CREATION AND REMOVAL BASED ON CONDITIONAL PROBABILITIES BETWEEN CLUSTERS

CROSS REFERENCE TO RELATED APPLICATIONS

This application is based on and hereby claims priority to German Application No. 10 2005 012 665.0 filed on Mar. 18, 2005, the contents of which are hereby incorporated by reference.

BACKGROUND OF THE INVENTION

1. Field of the Invention

The present invention relates to a method and a device for detecting clusters amongst data, in particular amongst data which denote complex products or services arranged into orders. Such data are characterized by the fact that they can be arranged in orders which contain some identical data. For example, identical components or parts of services may occur on a plurality of occasions if, in a business, the same product is sold on a plurality of occasions or identical components appear in different products, or if, in orders that are complicated to organize in the medical field, individual procedures, such as patient-related investigations or treatments and likewise care procedures in a hospital are included on a plurality of occasions. To achieve efficient organization, it then becomes necessary to detect correlated data amongst the data arranged in orders.

2. Description of the Related Art

The above problem occurs in particular in the computer-aided control of the running of a hospital, if in the field of hospital and patient management such services have to be organized, planned and controlled, such as the aforementioned investigations, general care procedures and also special rehabilitation procedures. Comparable problems also generally occur in the field of computer-aided production and order-processing in businesses.

To find such correlated groups within data, a method is described on pages 1-71 in *Independent Component Analysis* by Aapo Hyvärinen, Juha Karhunen and Erkki Oja, published by Wiley-Interscience in 2001, in which a search is made for independent components of the observed data. These components can include inter alia observed data such as economic indicators. Since the method was originally derived from signal theory, it cannot simply be applied as it is to binary sequences of data. Since in the present case, however, the data searched for are in fact correlated data in which certain components or services appear, or fail to appear, and it is these very data that are represented in binary form, the Independent Component Analysis method is not particularly useful in the present case.

Furthermore, the phenomenon of hierarchical clustering is known, which produces disjunctive clusters that do not have any components in common. In such a case, it is necessary to select a hierarchy level in which the clusters are defined.

The disadvantage of this is that the very clusters for which a search is made are those that contain some identical data and the above method does not therefore detect the desired clusters and the hierarchy level that is required is not easy to determine.

Another known method is called "Frequent Item Sets", which creates problems insofar as it generates too many highly correlated groups especially when less frequently occurring groups are also considered.

In "Probabilistic Latent Semantic Analysis" a search is made for statistically independent source data which create distributions across individual components. From these distributions a group can be defined via a threshold, the threshold not being easy to determine and it being necessary to establish a fixed number of source data.

SUMMARY OF THE INVENTION

An object of the present invention is therefore to provide a method and a device which allow clusters to be detected amongst groups of data, in particular data that describe orders such as services and products used in hospital and patient management and which are at least partially correlated.

A method according to the invention automatically identifies clusters amongst available data. Above all it allows the identification of certain clusters amongst orders that are correlated, such that standardization of the procedures can be achieved.

Advantageously, after forming new clusters Cn and before each repeat of the determination of a conditional probability $P(C_i|C'k)$, all the clusters that are contained in another cluster and are only included in an order at the same time as the cluster are removed.

In this way, the number of clusters is reduced by those that do not need to be considered separately since they only occur as part of another cluster which was newly formed on a previous occasion.

In an advantageous embodiment, after the formation of new clusters Cn and before each repeat of the determination of a conditional probability $P(C_i|C'k)$, all the clusters Cl that are contained in another cluster Cg are removed if the conditional probability $P(Cl|Cg)$ is greater than a fixed second threshold value S2.

Clusters Cl are no longer considered separately if the probability that they will occur in conjunction with another cluster is above a threshold value. As a result fewer relevant clusters are removed.

In an advantageous embodiment, after formation of new clusters Cn and before each repeat of the determination of a conditional probability $P(C_i|C'k)$, all the clusters Cl that occur in the orders less frequently than a third threshold value S3 are removed. In this way clusters which as a whole are only very few in number are removed, irrespective of the conditional probabilities or correlations.

The clusters can then be sorted according to the frequency of their occurrence in the orders. This makes it possible to find particularly relevant correlations.

The orders may be treatments and investigations and likewise care procedures in a computer-aided hospital and patient management system or similar system via products in the field of mobile communications.

In hospital and patient management it is necessary to guarantee a consistent quality of treatments that is as far as possible independent of human factors. To achieve this goal, standardization of treatments is aimed for. The method described here allows experts to automatically identify clusters, consisting of treatments, amongst existing data. The method can therefore be carried out after a new drug has been introduced for example, whereby it is possible to optimize treatments and procedures used for certain illnesses with the aid of the clusters that have been found.

BRIEF DESCRIPTION OF THE DRAWINGS

These and other objects and advantages of the present invention will become more apparent and more readily appreciated from the following description of an embodiment for detecting clusters amongst data arranged in orders in a computer, taken in conjunction with the accompanying drawings of which:

FIG. 1 is a block diagram of a system used to perform a method according to the invention; and FIG. 2 is a more detailed flowchart of a method according to the invention.

DETAILED DESCRIPTION OF THE PREFERRED EMBODIMENT

Reference will now be made in detail to the preferred embodiments of the present invention, examples of which are illustrated in the accompanying drawings, wherein like reference numerals refer to like elements throughout.

FIG. 1 is a diagram showing the basic sequence of a method according to the invention. From a database 1 having data arranged in orders, in this case data describing services and products used in hospital and patient management, the orders are converted in a conversion unit 2 into a binary format. Then a method according to the invention is carried out in a cluster unit 3 and the clusters found are shown on a screen 4.

FIG. 2 is a more detailed flowchart of a method according to the invention. In a first operation 1, first clusters are formed. Let us assume that the following notations are agreed on for the further description of the method:
A1, A2, etc.: Orders
K1, K2, etc.: Data that describe services and products of hospital and patient management (components)
$C_i$, $C'_k$: Clusters i, and k Then the following 10 orders A1-A10 can be set out in table form together with components K1-K4:

|     | K1 | K2 | K3 | K4 |
|-----|----|----|----|----|
| A1  | 1  | 0  | 0  | 1  |
| A2  | 1  | 1  | 0  | 0  |
| A3  | 0  | 0  | 0  | 0  |
| A4  | 0  | 1  | 1  | 0  |
| A5  | 0  | 0  | 0  | 0  |
| A6  | 0  | 0  | 1  | 0  |
| A7  | 1  | 0  | 0  | 0  |
| A8  | 1  | 0  | 1  | 1  |
| A9  | 0  | 0  | 0  | 0  |
| A10 | 0  | 0  | 1  | 0  |

Here components K1-K4 stand for drugs, treatments or care procedures, for example. Then, in a first operation 1, the following first four clusters are formed:

|    | K1 | K2 | K3 | K4 |
|----|----|----|----|----|
| C1 | 1  | 0  | 0  | 0  |
| C2 | 0  | 1  | 0  | 0  |
| C3 | 0  | 0  | 1  | 0  |
| C4 | 0  | 0  | 0  | 1  |

Each of these first clusters C1-C4 contains only one component. In a second operation 6, the conditional probability $P(C_i|C'_k)$ is computed for all instances of i, k. For the values i=1, k=2, cluster C2 occurs in orders A2 and A4. But C1 occurs only in A2. Thus $P(C1|C'2)=0.5$ is the probability, that C1 will occur on the additional condition that C2 also occurs. Hence for all the possible values of i, k between 1 and 4 the results are:

|    | C'1  | C'2 | C'3  | C'4  |
|----|------|-----|------|------|
| C1 | 1    | 0.5 | 0.25 | 1    |
| C2 | 0.25 | 1   | 0.25 | 0    |
| C3 | 0.25 | 0.5 | 1    | 0.5  |
| C4 | 0.5  | 0   | 0.25 | 1    |

In a first branch 7, which now follows, the computer is asked whether one of the conditional probabilities $P(C_i|C'_k) > S1$, S1 being a fixed threshold, in this case for example 0.8. This is the case with $P(C1|C'4)$ and, in a third operation 8, a new cluster C5 is formed from C4 and C1, the cluster containing the components of C1 and C4. A new cluster table is thus created:

|    | K1 | K2 | K3 | K4 |
|----|----|----|----|----|
| C1 | 1  | 0  | 0  | 0  |
| C2 | 0  | 1  | 0  | 0  |
| C3 | 0  | 0  | 1  | 0  |
| C4 | 0  | 0  | 0  | 1  |
| C5 | 1  | 0  | 0  | 1  |

In a fourth operation 9 all the clusters which are contained in an identical form in another cluster and which always appear only in conjunction with the cluster are removed. This means removing each redundant cluster that is a proper subset of an encompassing cluster and does not appear in any of the orders independently from the encompassing cluster. In the example above, clusters C1 and C4 are contained in an identical form in cluster C5. Cluster C1 appears in orders A1, A2, A7 and A8, while cluster C4 appears in orders A1, A8 and cluster C5 appears in orders A1 and A8. Therefore, cluster C4 only appears in conjunction with cluster C5 and is deleted. Hence the following current clusters are C1, C2, C3, C5:

|    | K1 | K2 | K3 | K4 |
|----|----|----|----|----|
| C1 | 1  | 0  | 0  | 0  |
| C2 | 0  | 1  | 0  | 0  |
| C3 | 0  | 0  | 1  | 0  |
| C5 | 1  | 0  | 0  | 1  |

In a fifth operation 10 all the clusters Cl which are contained in an identical form in another cluster Cg, where Cl is a proper subset of Cg, and whose conditional probability P(Cl|Cg) for an occurrence in conjunction with the cluster is greater than a second threshold value S2 are removed, as cluster(s) Cl are substantially redundant, given the encompassing cluster(s) Cg. In the present example, this is not the case for any cluster.

In a sixth operation 11 all the clusters whose frequency of occurrence in number in the orders is below a threshold value S3 are removed. In the present example, this does not apply to any cluster.

In the second branch 12 the computer is asked whether any new clusters have been formed. This is true of cluster C5. The method therefore goes back to the second operation 6 and once again computes conditional probabilities $P(C_i|C'_k)$. For example, for i=3, k=5 the result is that cluster C5 occurs in orders A1 and A8. C3 occurs only in A8 of the above orders. Hence $P(C3|C'5)=0.5$. Hence for all values of i, k the following table applies:

|    | C'1  | C'2 | C'3  | C'5 |
|----|------|-----|------|-----|
| C1 | 1    | 0.5 | 0.25 | 1   |
| C2 | 0.25 | 1   | 0.25 | 0   |
| C3 | 0.25 | 0.5 | 1    | 0.5 |
| C5 | 0.5  | 0   | 0.25 | 1   |

Hence, in the first branch 7 it follows that P(C1|C'5)>0.8 and a new cluster C6 would be formed in the third operation 8, the cluster being identical to C5, however. Thus no more new clusters are formed and in the second branch 12 the process comes to a conclusion. The resulting clusters are:

|    | K1 | K2 | K3 | K4 |
|----|----|----|----|----|
| C1 | 1  | 0  | 0  | 0  |
| C2 | 0  | 1  | 0  | 0  |
| C3 | 0  | 0  | 1  | 0  |
| C5 | 1  | 0  | 0  | 1  |

The method can also be used to identify standardized platforms in other products such as base stations for mobile communications networks, which consist of many thousands of components. In such products a plurality of different components essentially perform an identical function. Distribution and development therefore try as far as possible to use identical components in order to reduce the number of different components and hence the costs of distribution, maintenance and development.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV*, 69 USPQ2d 1865 (Fed. Cir. 2004).

What is claimed is:

1. A method for detection of clusters amongst data arranged in orders in a computer, at least some of the orders containing components including at least one of services and products, at least some components in more than one of the orders, comprising:
    initially forming clusters, each containing only one component being one of a service and a product, with each cluster containing a different component than all other clusters;
    determining a conditional probability $P(C_i|C'_k)$ for a first cluster $C_i$ included in an order containing components on condition that a second cluster $C'_k$ is included in the order containing components, across all instances of i and for all instances of k, where i and k run through all of the clusters in the orders;
    adding to the clusters by forming each new cluster $C_n$ containing the components of existing clusters $C_i$ and $C'_k$ for which the conditional probability $P(C_i|C'_k)$ is greater than a first threshold value; and
    repeating said determining and adding until no new cluster is formed.

2. A method according to claim 1, further comprising, after said adding and before repeating said determining, removing each redundant cluster that is a proper subset of an encompassing cluster and does not appear in any of the orders independently from the encompassing cluster.

3. A method according to claim 1, wherein no new cluster is formed when each cluster formed in one repetition of said adding already exists.

4. A method for detection of clusters amongst data arranged in orders in a computer, at least some of the orders containing components including at least one of services and products, at least some components in more than one of the orders, comprising:
    initially forming clusters, each containing only one component being one of a service and a product, with each cluster containing a different component than all other clusters;
    determining a conditional probability $P(C_i|C'_k)$ for a first cluster $C_i$ included in an order containing components on condition that a second cluster $C'_k$ is included in the order containing components, across all instances of i and for all instances of k, where i and k run through all of the clusters in the orders;
    adding to the clusters by forming each new cluster $C_n$ containing the components of existing clusters $C_i$ and $C'_k$ for which the conditional probability $P(C_i|C'_k)$ is greater than a first threshold value; and
    repeating said determining and adding until no new cluster is formed and after said adding and before repeating of said determining, removing each redundant cluster Cl that is a proper subset of an encompassing cluster Cg if the conditional probability $P(Cl|Cg)$ is greater than a fixed second threshold value.

5. A method according to claim 4, further comprising, after said adding and before repeating said determining, removing each infrequent cluster that occurs in the orders less frequently than a third threshold value.

6. A method according to claim 5, further comprising sorting the clusters according to frequency of occurrence in the orders.

7. A method according to claim 6, wherein the orders are at least one of treatments, investigations and care procedures in a computer-aided hospital and patient management system.

8. A method according to claim 6, wherein the orders are for mobile communications products.

9. At least one computer-readable medium storing instructions that when executed control a computer to perform a method for detection of clusters amongst data arranged in orders, at least some of the orders containing components including at least one of services and products, at least some components in more than one of the orders said method comprising:
    initially forming clusters, each containing only one component, being one of a service and a product, with each cluster containing a different component than all other clusters;
    determining a conditional probability $P(C_i|C'_k)$ for a first cluster $C_i$ included in an order containing components on condition that a second cluster $C'_k$ is included in the order containing components, across all instances of i and for all instances of k, where i and k run through all of the clusters in the orders;
    adding to the clusters by forming each new cluster $C_n$ containing the components of existing clusters $C_i$ and $C'_k$ for which the conditional probability $P(C_i|IC'_k)$ is greater than a first threshold value; and
    repeating said determining and adding until no new cluster is formed.

10. At least one computer-readable medium according to claim 9, said method further comprising, after said adding and before repeating said determining, removing each redundant cluster that is a proper subset of an encompassing cluster and does not appear in any of the orders independently from the encompassing cluster.

11. At least one computer-readable medium storing instructions that when executed control a computer to perform a method for detection of clusters amongst data arranged in orders, at least some of the orders containing components including at least one of services and products, at least some components in more than one of the orders, said method comprising:

initially forming clusters, each containing only one component, being one of a service and a product, with each cluster containing a different component than all other clusters;

determining a conditional probability $P(C_i|C'_k)$ for a first cluster $C_i$ included in an order containing components on condition that a second cluster $C'_k$ is included in the order containing components, across all instances of i and for all instances of k, where i and k run through all of the clusters in the orders;

adding to the clusters by forming each new cluster $C_n$ containing the components of existing clusters $C_i$ and $C'_k$ for which the conditional probability $P(C_i|C'_k)$ is greater than a first threshold value; and repeating said determining and adding until no new cluster is formed and after said adding and before repeating said determining, removing each substantially redundant cluster $C_l$ that is a proper subset of an encompassing cluster $C_g$ if the conditional probability $P(C_l|C_g)$ is greater than a fixed second threshold value.

12. At least one computer-readable medium according to claim 11, said method further comprising, after said adding and before repeating said determining, removing each infrequent cluster that occurs in the orders less frequently than a third threshold value.

13. At least one computer-readable medium according to claim 12, said method further comprising sorting the clusters according to frequency of occurrence in the orders.

14. At least one computer-readable medium according to claim 13, wherein the orders are at least one of treatments, investigations and care procedures in a computer-aided hospital and patient management system.

15. At least one computer-readable medium according to claim 14, wherein the orders are for mobile communications products.

16. A control system for planning and controlling treatments, investigations and care procedures in a hospital, comprising:

a user network;

a database storing data arranged in orders, at least some of the orders containing components including at least one of services and products, at least some components in more than one of the orders;

at least one computer, connected to said database via said user network, executing a program initially forming clusters, each containing only one component with each cluster containing a different component than all other clusters; determining a conditional probability $P(C_i|C'_k)$ for a first cluster $C_i$ included in an order containing components on condition that a second cluster $C'_k$ is included in the order containing components, across all instances of i and for all instances of k, where i and k run through all of the clusters in the orders; adding to the clusters by forming each new cluster $C_n$ containing the components of existing clusters $C_i$ and $C'_k$ for which the conditional probability $P(C_i|C'_k)$ is greater than a first threshold value; and repeating the determining and adding until no new cluster is formed and after said adding and before repeating said determining, removing each substantially redundant cluster $C_l$ that is a proper subset of an encompassing cluster $C_g$ if the conditional probability $P(C_l|C_g)$ is greater than a fixed second threshold value; and at least one output device to output information representing the existing clusters when the repeating ends.

\* \* \* \* \*